DILUTING LIQUID SAMPLES

BACKGROUND OF THE INVENTION

This invention relates to an automatic diluter and more particularly to a diluter which permits aspiration of a very small sample and subsequent dilution of the sample at very high ratios.

Automatic diluters are available which provide for the aspiration of a predetermined quantity of a sample fluid, followed by the discharge of the measured sample together with a predetermined quantity of diluent. While there are many particular constructions of diluters of this class, in each the change of diluent involves the flushing of various hydraulic lines and connections in order to prevent diluent contamination by a previously used diluent. Such diluters typically require a valve assembly for switching purposes between aspirate and dispense modes of operation, the valve assembly being a relatively expensive sub-assembly of the diluter and being a source of possible error.

Another type of apparatus provides a self-contained diluent unit which is removable from the dispenser for subsitution by another diluent unit containing a different type of diluent. A dispensing piston within the diluent unit is driven to dispense diluent through an outlet for diluting a liquid sample which has been measured using other apparatus. The operation of this class of apparatus, therefore, is less useful than an automatic diluter capable of both measuring the sample and dispensing the diluent.

Among the objects of the present invention may be noted the provision of an automatic diluter, and of a diluent module incorporated therein, which facilitates the automatic aspiration of a relatively small sample of liquid and the dilution of that sample with a relatively large volume of diluent, wherein the diluent module is removable from the remainder of the diluter and is interchangeable with other such modules.

Further objects include the provision of an automatic diluter which eliminates hydraulic lines and valving, which permits recovery of unused diluent, and which permits a convenient and precise selection of a wide variety of dilution ratios.

SUMMARY OF THE INVENTION

Briefly, a diluter in accordance with the present invention comprises a diluent cylinder having an outlet and a conduit communicating with that outlet. A diluent dispensing piston within the cylinder is driven by first drive means capable of moving the diluent piston toward the cylinder outlet in order to force the diluent from the cylinder, through the outlet, and into the conduit. A second piston, of relatively smaller cross section than the diluent piston, is supported in a bore in the diluent piston and is movable with respect to the diluent piston. A second drive means is capable of moving the second piston independently of the diluent piston for a relatively short distance in a direction away from the cylinder outlet. Thus, movement of the second, smaller piston enables aspiration into the conduit of a relatively small sample of a liquid and subsequent movement of the diluent piston toward the outlet enables ejection from the conduit of that small sample along with a relatively large quantity of diluent.

Preferably, the apparatus comprises a control and drive unit and a separable diluent module. The drive unit includes a first drive rod releasably engagable with the diluent piston and a second drive rod releasably engagable with the second piston. The first drive rod is driven by a stepping motor controlled by a motor control unit which includes a counter for counting a predetermined number of clock pulses and for causing an incremental rotation of the stepping motor for each pulse up to the predetermined number. The motor control unit further includes means for selecting the total number of pulses countable, thus facilitating adjustment of the stroke of the diluent piston and, consequently, the quantity of diluent dispensed by the apparatus.

Other objects, features, and advantages of the invention will be in part apparent and in part pointed out hereinafter in connection with the description of an illustrative embodiment shown in the accompanying drawings.

DETAILED DESCRIPTION OF A PARTICULAR PREFERRED EMBODIMENT

Figure 1:
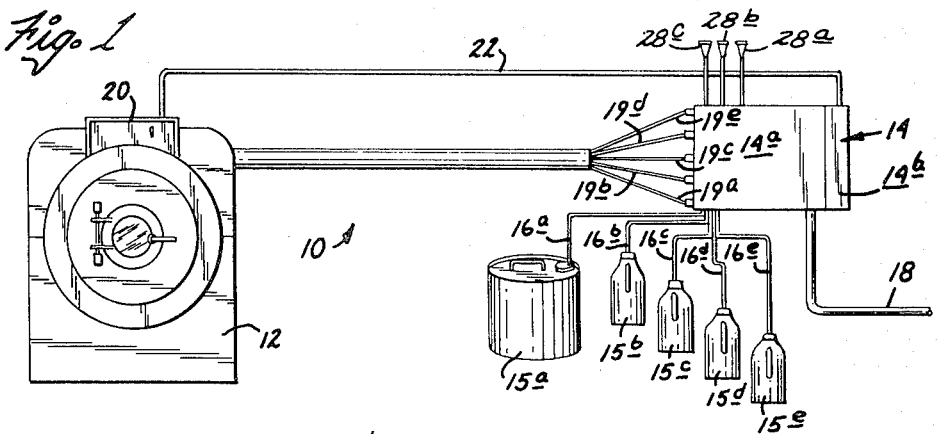
FIG. 1 is a front elevation of a diluter constructed in accordance with the present invention.

Referring first to FIG. 1, there is shown a diluter consisting of a control and drive unit 11 and a diluent module 13 secured to a horizontal surface 15 of the unit 11 by a retainer clip 17. Controls 19, 21, 23, 25, 27, and 29 and an indicator 31 are mounted on the front faces 33 and 35 of the unit 11 and have functions discussed below in connection with FIGS. 2 and 4.

Figure 2:
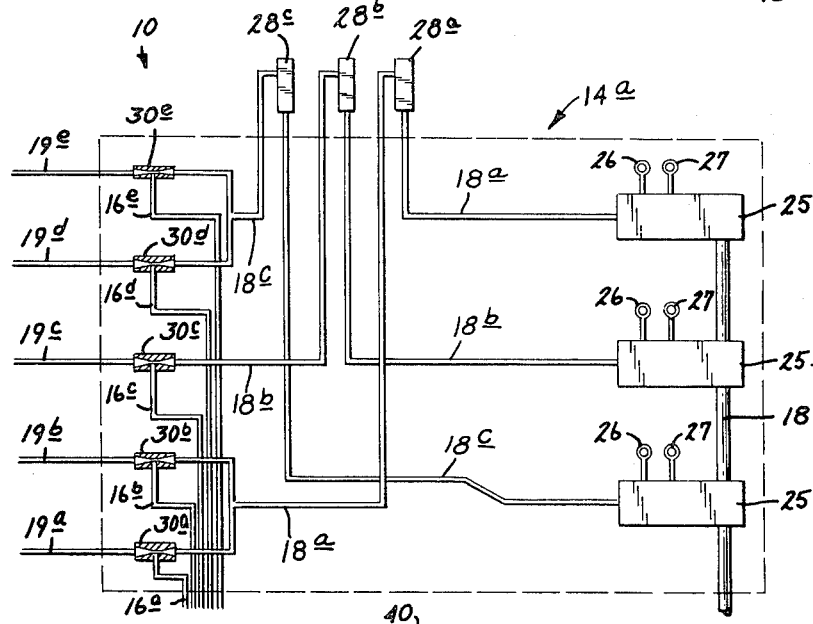
FIG. 2 is a view taken at 2—2 of FIG. 1.
Figure 1:
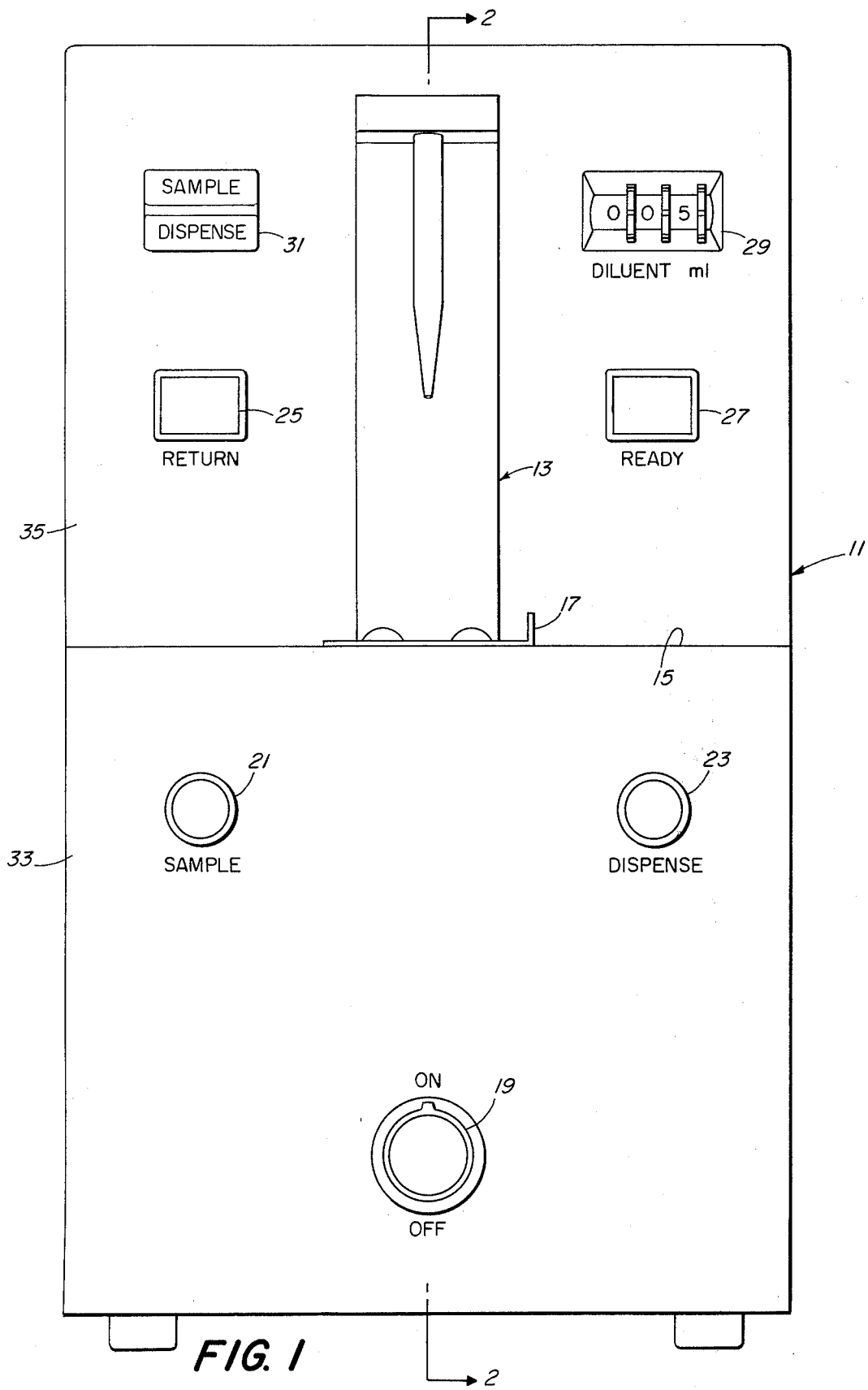
Figure 2:
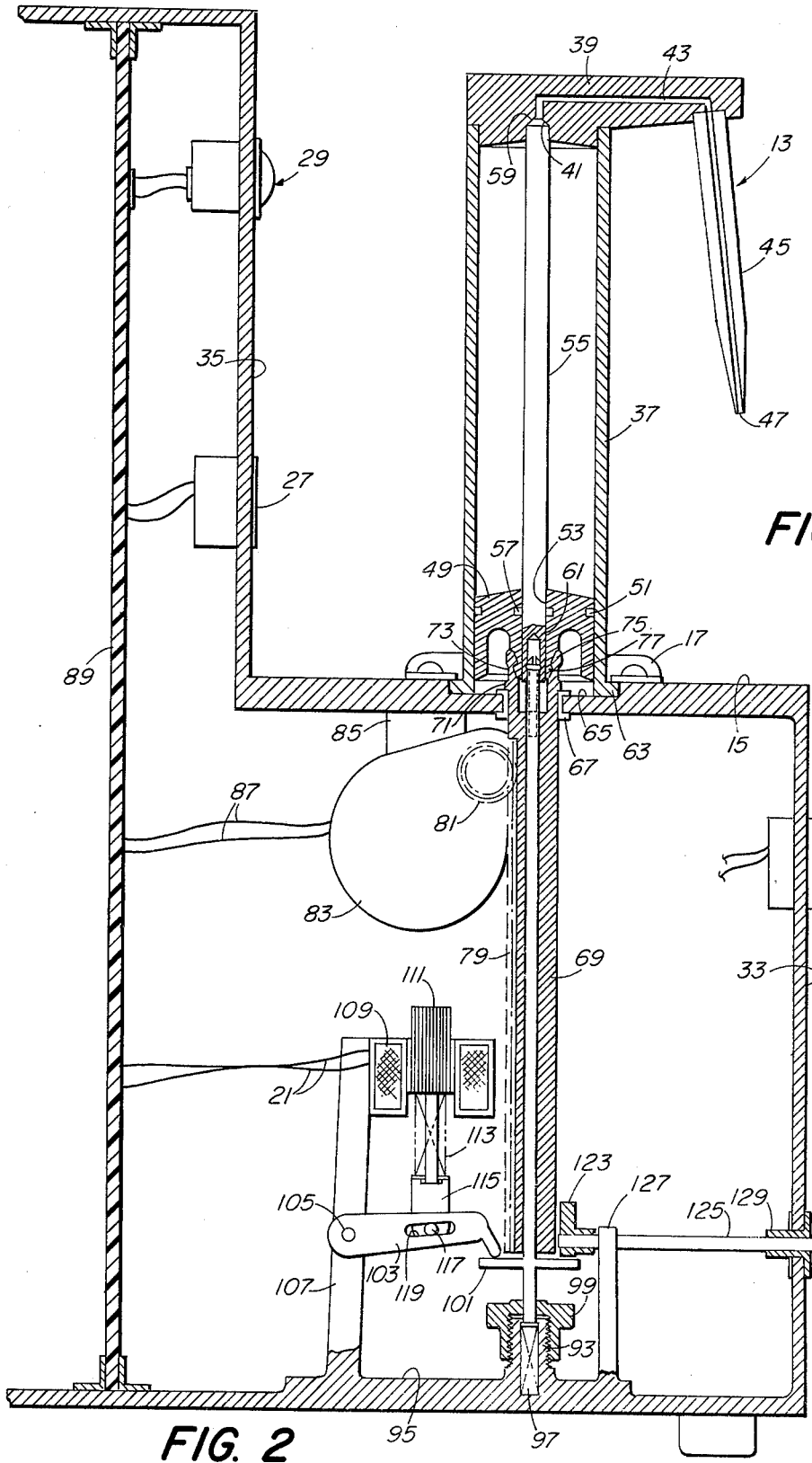

Referring now to FIG. 2, the diluent module 13 comprises a cylinder 37, which acts as a diluent reservoir, and a cap assembly 39 secured to one end of the cylinder 37 and defining an outlet 41. An internal conduit 43 in the cap assembly 39 connects the outlet 41 with a probe or spout 45 which tapers to a generally downwardly directed outlet 47 of its own. A diluent dispensing piston 49 is provided within the cylinder 37 and engages the internal walls of the cylinder. A resilient sealing member 51 in an external groove in the piston 49 assists in maintaining a leak-proof fit of the piston 49 with the wall of cylinder 37. A central bore 53 in the piston 49 receives a second, smaller piston 55 which is slidable within the bore 53. A resilient sealing member 57 is provided in a circular recess in the surface of the bore 53 to seal against the surface of piston 55. The piston 55 has a length at least as long as the length of cylinder 37, thereby enabling a beveled end surface 59 thereof to engage a matching bevel of the outlet 41, while the opposite end 61 of the piston 55 remains within bore 53 below the seal member 57. A flange 63 at the end of cylinder 37 opposite the cap assembly 39 is sized to be received in a recess 65 in the horizontal surface 15 of the control and drive unit and to be engaged by the retainer clip 17 for securing the diluent module 13 to the unit 11.

Still referring to FIG. 2, a bearing member 67, mounted in a circular opening in horizontal surface 15 which is centered in recess 65, serves as a guide, and a stop, for a first, hollow, vertically disposed drive rod 69. A coupling chuck at the upper end of drive rod 69 projects above the recess 65 owing to a shoulder 71 of the drive rod which engages the upper surface of bearing member 67, thereby defining a stop in the downward motion of the drive rod. The coupling chuck consists of a portion 73 of the drive rod 69 having a reduced wall thickness, thereby facilitating radial flexibility at that point, and an inwardly facing annular lip 75, adjacent the portion 73, engagable with a mating, externally facing, annular lip 77 of the piston 49. A vertically disposed gear rack 79 is recessed in the external surface of drive rod 69 and engages a pinion gear 81 secured to the rotary member (not shown) of a stepping motor 83 which is supported within the unit 11 by a bracket 85. Electrical leads 87 extend between the motor 83 and a circuit board 89 supported within the unit 11.

A second drive rod 91 is coaxial with, and extends through the hollow interior of, drive rod 69. The second drive rod 91 extends downwardly below the lower end of the first drive rod 69 and fits into a hollow stud 93 projecting upwardly from the floor 95 of the drive unit 11. A compression spring 97 within the stud 93 biases the second drive rod 91 upwardly. A threaded cap 99, having an opening for receiving the drive rod 91, engages mating threads on the exterior of stud 93 to provide an adjustable stop which limits the downward motion of the drive rod 91 when a radial flange 101, integral with the drive rod 91, strikes the upper surface of the cap 99. A cam lever 103 is pivotally secured by pin 105 to a structural member 107 projecting upwardly from the floor 95 of the unit 11 and bears against the flange 101 for driving the drive rod 91 downwardly against the upward biasing force of the spring 97. The cam lever 103 is driven by a solenoid coil 109, also secured to the member 107, having an armature 111 coupled through a clevis spring 113 to a member 115 having a pin 117 disposed within a slot 119 of the cam lever 103. This arrangement causes cam lever 103 to pivot about pin 105 in response to the linear movement of armature 111. Leads 121 extend from the solenoid coil 109 to the circuit board 89.

Also engagable with flange 101 is an eccentric wheel 123 mounted on a shaft 125 which is supported for rotation in a member 127 projecting upwardly from the floor 95 adjacent the flange 101 and a bushing 129 mounted in the front face 33 of unit 11. The control knob 19 is secured to the shaft 125 for rotation therewith. Rotation of the control knob 19 causes the eccentric wheel 123 to rotate thereby camming the flange 101, and the drive rod 91, downwardly a short distance against the force of biasing spring 97. As discussed in detail below, when the drive rod 91 is engages with the piston 55 of the diluent module 13, this movement causes the beveled upper surface 59 of the piston 55 to disengage from the outlet 41 of the diluent cylinder 37.

Figure 3:
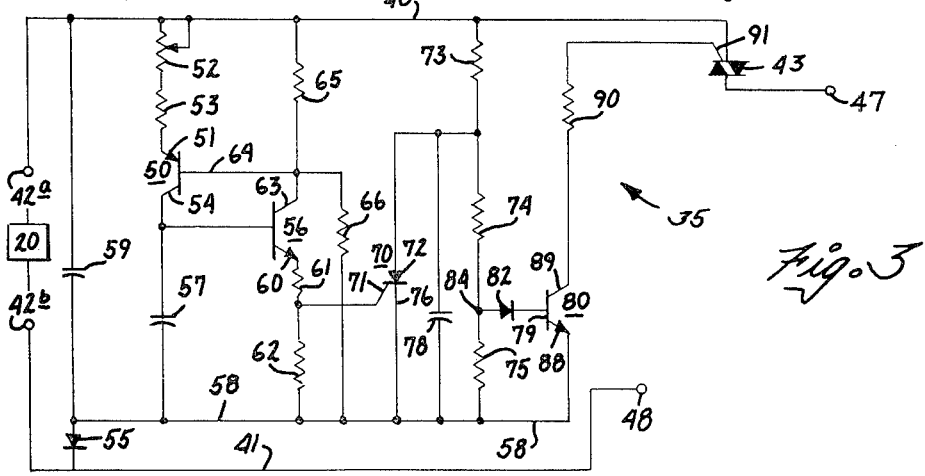
FIGS. 3A and 3B are enlarged sectional views of the releasable connection of the sampling piston and its drive rod.
Figure 3A:
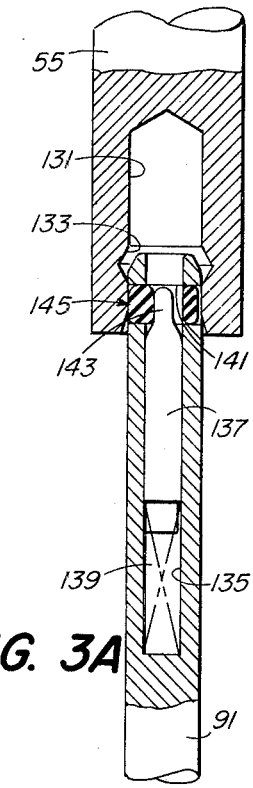
Figure 3B:
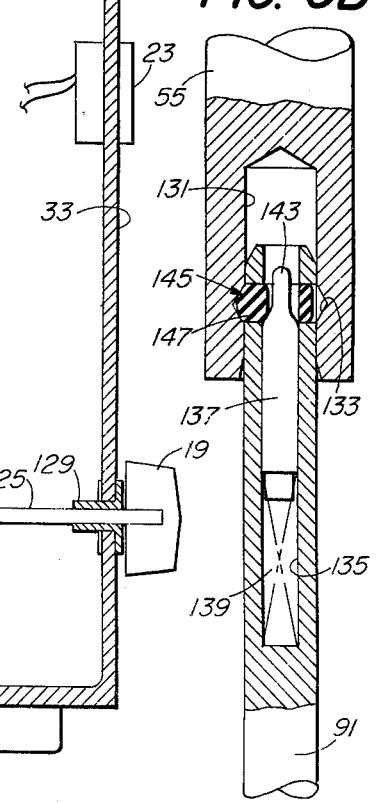

The coupling of the upper end of the second drive rod 91 with the lower end of piston 55 will be best understood by reference to FIGS. 3A and 3B. An axial bore 131 is provided in the lower end of piston 55, as is an annular radial groove 133 in the internal surface of the bore 131. A bore 135 is also provided in the upper end of piston 91 and a plunger 137, upwardly biased by plunger spring 139, is disposed within the bore 135. A transverse bore 141 in the piston 91 intersects the bore 135 adjacent the head 143 of the plunger 137. An eccentric latch pellet 145 is disposed for transverse sliding motion in the bore 141. As best seen in FIG. 3B, the upward force of plunger 137 biases the latch pellet 145 to an orientation in which a hemispherical lobe 147 protrudes beyond the outer surface of the piston 91. In that orientation, the lobe 147 may engage the groove 133 thereby connecting the drive rod 91 to the piston 55. The insertion of the drive rod 91 into the bore 131 displaces the hemispherical lobe 147 against the influence of the plunger biasing spring 139 (see FIG. 3A). By choosing the spring 97, at a lower end of the drive rod 91, to have a substantially greater compressive force than the plunger spring 139, the drive rod 91 will not move downwardly as the surface of bore 131 bears upon the latch pellet 145 causing a downward force against spring 139 to be transmitted to the drive rod 91.

Figure 4:
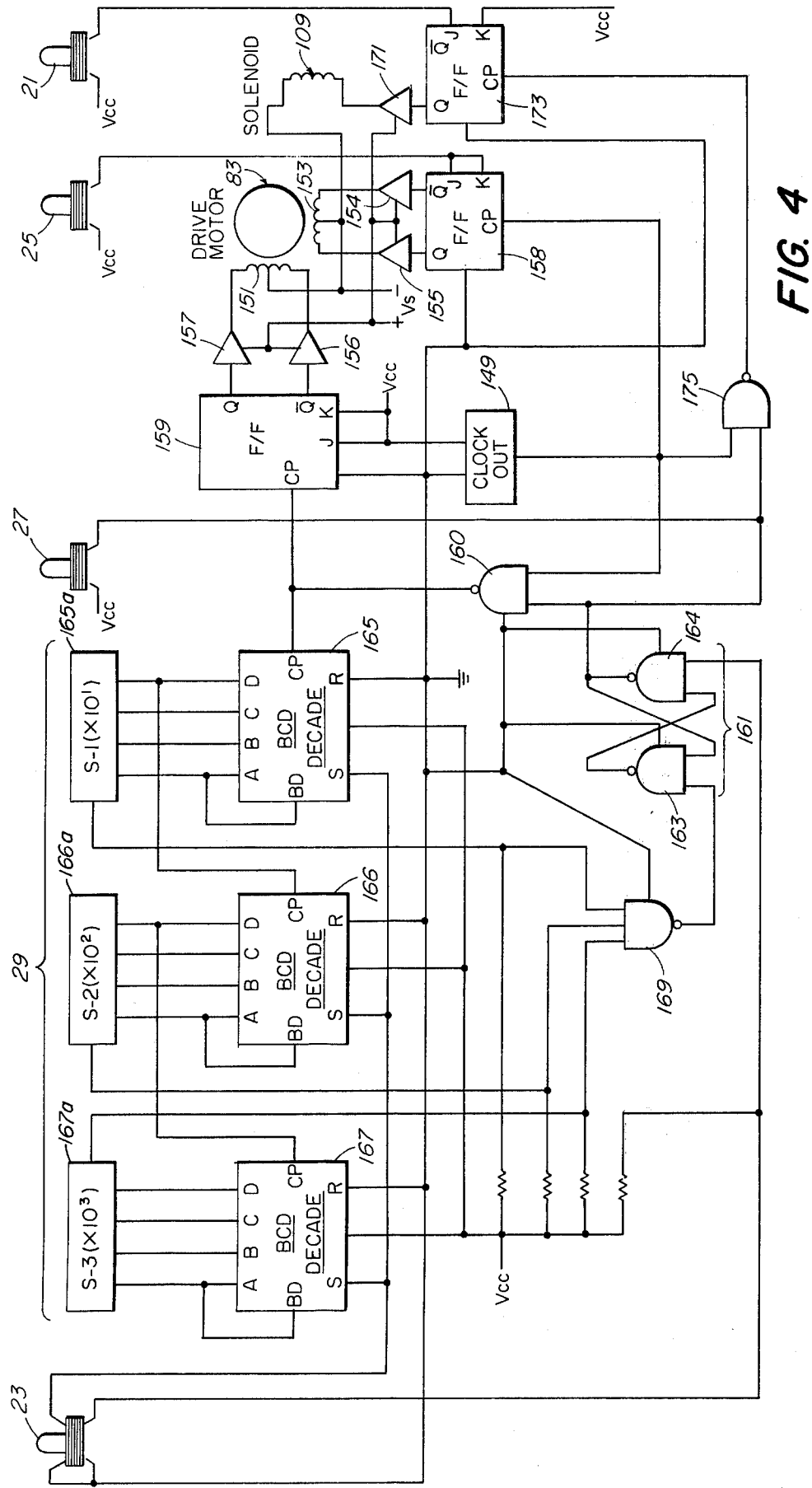
FIG. 4 is a logic diagram of the control and drive unit of the diluter of FIGS. 1 and 2.

FIG. 4 is a logic diagram of the circuitry incorporated in the control and drive unit 11. The drive motor 83 has a pair of center-tapped drive windings 151 and 153 for producing rotation in the forward and reverse directions respectively. The opposite ends of these windings are driven, through respective J-K flip-flop circuits 158 and 159. A clock oscillator 149 provides a continuous pulse train output signal. This signal is applied directly to the clock input of flip-flop 158 and, through a NAND gate 160, to the clock input of flip-flop 159. Passage of the clock pulses through the gate 160 is controlled by an R-S flip-flop 161 comprising a pair of NAND gates 163 and 164.

For generating a pulse string of predetermined length, the control apparatus of FIG. 4 employs a preset counter comprising three BCD decade counters 165–167, together with respective decade selection switches 165a–167a which together make up the diluent volume selection switch 29. Clock pulses passed by the gate 160 are applied to the string of counters 165–167 as well as to the motore drive circuitry. When each decade counter reaches the value determined by the setting of the respective switch 165a–167a, an output signal is passed by the switch. These three output signals are combined in a NAND gate 169 to generate a signal which resets the flip-flop 161 when there is an overall match between the value held in the counter and the setting of the switch 29.

The flip-flop 161 may be placed in its set state to initiate a dispense cycle by pressing the push-button switch 23 which is interconnected with the NAND gate 164 as shown. The operation of the switch 23 also resets the counters 165–167, the counters being released to commence counting when the button is released. Accordingly, each time the push-button switch 23 is momentarily operated, a pulse string is initiated which continues until the number of pulses counted equals the value set into the switches 165a–167a.

The drive motor 83 may be continuously energized in the forward direction by depressing the push-button switch 27 which opens the gate 160 independently of the state of the flip-flop 161. Continuous operation of the drive motor 83 in the reverse direction is obtained by depressing the push-button switch 25 which is interconnected with the J and K inputs of the flip-flop 158 so that, when the button is operated, the flip-flop will respond to clock input pulses and energize the reverse winding 153. As will be understood by those skilled in the art, the J-K flip-flop 158 is otherwise unresponsive to the clock signal continuously applied thereto. The solenoid 109 is controlled through a driver amplifier 171, by a J-K flip-flop 173. The solenoid may be energized by depressing the push-button switch 21 which is interconnected with the J input of the flip-flop. When push-button switch 21 is released, the solenoid will remain energized in the absence of any pulse signals applied to the clock input of the flip-flop. Such clock pulses are applied, through NAND gate 175, only when the motor is again energized. Accordingly, when the solenoid is energized to aspirate a sample, the sample will not be immediately ejected when the control 21 is released but rather is ejected together with the diluent.

In the operation of the apparatus as described above, a diluent module 13, having its cylinder 37 filled with the module vertically into the recess 65 in the surface 15 of the unit 11 and applying the necessary downward pressure to cause the radial flexing of the reduced thickness portion 73 of drive rod 69 and additionally, the displacement of latch pellet 145 with the attendent compression of plunger spring 139. This manual downward pressure causes the engagement of each of the drive rods with the respective pistons 49 and 55. With the cylinder flange 63 seated in the recess 65, the retainer clip 17 is pressed into place to securely retain the module 13 on the unit 11.

Prior to use of the module 13, the beveled upper surface 59 of the sample aspirating piston 55 engages the outlet 41 to form a valve blocking the outlet, thereby preventing leakage of diluent through the outlet 41, conduit 43, and spout 45 during the shipping or storage of the module 13. Prior to the diluting sequence of operation of the apparatus, this valve is opened by merely rotating the control knob 19 to cause the eccentric wheel 123 to depress drive rod 91 and the attached piston 55 a small amount, thereby opening the outlet 41 of cylinder 37. With a container in place beneath the outlet 47 of spout 45, the conduit 43 and spout 45 are filled with diluent by momentarily depressing the ready control 27 which is connected, as will be clear to those skilled in the art from the schematic diagram of FIG. 4, to operate the stepping motor 83 and thus drive the diluent piston 49.

With the conduit 43 and spout 45 filled with diluent, the outlet 47 of spout 45 is submerged in a container of the sample fluid and the sample aspirate control 21 is pressed. This control energizes the solenoid 109 and thereby causes the downward stroke of piston 55 for a distance determined by the position of the stop 99. This causes the aspiration into the spout 45 of a volume of sample fluid equal to the volume of piston 55 withdrawn from the cylinder. Because of the small diameter of piston 55 and the small downward stroke permitted by the stop 99, a very small volume of sample can be aspirated into spout 45. The volume aspirated can be precisely determined by adjusting the stroke of the piston 55 using the adjustable stop 99.

Next, a container for the diluted sample is placed beneath the outlet 47 of probe 45 and the dispense control 23 is pressed. As described with reference to FIG. 4, this control causes the operation of motor 83 for predetermined number of incremental rotations, the number being equal to that set by the diluent quantity selection switch 29. The displacement of the piston 49 for each incremental rotation of the rotary member of the motor 83 can be determined for any given motor and gearing arrangement. Accordingly, by a suitable choice of the dimensions of piston 49 and cylinder 37 in relation to the gearing, the control 31 can be made to read directly in milliliters. The arrangement described, therefore, permits the convenient and precise selection of the desired volume of diluent to be dispensed by the apparatus.

When the diluent has been dispensed, the module 13 may be removed and another installed in the manner described above. Alternatively, the empty module 12 may be refilled by submerging the outlet 47 of the probe 45 in a container of diluent and depressing the piston return control 25 which causes the piston 49 to be driven downwardly by the reverse rotation of the motor's rotary member. This motion of the piston 49 aspirates diluent from the container into the cylinder 37.

In view of the foregoing, it may be seen that the several objects of the present invention are achieved and other advantageous results have been attained.

As various changes could be made in the above constructions without departing from the scope of the invention, it should be understood that all matter contained in the above description, or shown in the accompanying drawings, shall be interpreted as illustrative and not in a limiting sense.

I claim:

1. Apparatus for diluting a sample of liquid with a diluent comprising
    a diluent cylinder having an outlet at one end thereof,
    a conduit communicating with said cylinder outlet,
    a diluent dispensing piston within said cylinder of substantially the same cross section as said cylinder and having a bore therethrough, and a second piston of relatively smaller cross section than said diluent dispensing piston supported in said bore for movement with respect to said diluent dispensing piston,
    piston drive means comprising first means for moving said diluent dispensing piston toward said cylinder outlet substantially the full length of said cylinder to dispense a large fraction of diluent contained in said cylinder, and second means for moving said second piston relative to said diluent dispensing piston in a direction away from said cylinder outlet for a distance must less than the full length of said cylinder;
    whereby movement of said second, smaller piston enables aspiration of relatively small sample of liquid into said conduit and subsequent movement of said diluent dispensing piston toward said outlet enables ejection from said conduit of said relatively small sample along with a relatively large quantity of diluent.

2. The apparatus of claim 1 wherein said first and second pistons are coaxial.

3. The apparatus of claim 2 wherein said cylinder outlet is coaxial with said second piston, thereby enabling said second piston to block said cylinder outlet, to prevent premature delivery of diluent to said conduit, prior to said movement of said second piston away from said cylinder outlet.

4. The apparatus of claim 1 wherein said first piston has a cross section greater than ten times the cross section of said second piston.

5. The apparatus of claim 1 wherein said first means for moving said first piston comprise a stepping motor having an incrementably rotatable rotary member connected to linearly drive said first piston and motor control means for causing a predetermined number of incremental rotations of said rotary member.

6. The apparatus of claim 5 wherein said motor control means further comprise means for selecting said predetermined number of incremental rotations, thereby selecting the stroke of said first piston and the quantity of diluent dispensed by the apparatus.

7. A diluent module for use with a drive means to provide an apparatus for diluting a sample of liquid with a diluent, the diluent module comprising a cylinder for holding diluent, an outlet at one end of said cylinder, a dispensing spout, a conduit interconnecting said outlet and said dispensing spout, a first piston within said cylinder engaging the walls thereof in a substantially leak-proof engagement, said first piston having a surface with a bore therethrough facing said outlet and a reverse surface for receiving driving force from said drive means to move said first piston toward said outlet, and a second piston of smaller cross section than said first piston supported in leak-proof engagement in said bore for movement relative to said first piston, said second piston having a surface facing said outlet and a reverse surface having coupling means for engagement with said drive means thereby enabling movement of said second piston in direction away from said outlet;

whereby movement of said second, smaller piston in a direction away from said outlet enables aspiration of a relatively small sample of liquid into said spout and subsequent movement of said first, larger piston toward said outlet enables the dispensing from said spout of said relatively small sample of liquid along with a relatively large quantity of diluent.

8. The diluent module of claim 7 wherein said first piston has a cross section of at least about ten times the cross section of said second piston.

9. The diluent module of claim 7 wherein said cylinder outlet is coaxial with said second piston, thereby enabling said second piston to block said cylinder outlet, to prevent premature delivery of diluent to said conduit, prior to said movement of said second piston away from said cylinder outlet.

10. The diluent module of claim 9 wherein said outlet is bevelled and said first piston surface that faces outlet has a matching bevel, thereby facilitating the blocking of said outlet by said second piston.

11. The diluent module of claim 7 wherein said coupling means comprise a detent in an internal bore in said reverse surface of said second piston, said detent disposed to receive a bead on a drive rod of said drive means which is insertable into said bore.

12. Apparatus for diluting a sample of liquid with a diluent comprising a drive unit and diluent module releasably connectable to said drive unit, said diluent module comprising a diluent cylinder having means engagable with said drive unit for releasably connecting said diluent module to said drive unit, an outlet at one end of said cylinder, a dispensing spout, a conduit interconnecting said outlet and said dispensing spout, a first piston within said cylinder coaxial therewith and engaging the walls thereof in a substantially leak-proof engagement, said first piston having a surface facing said outlet and a reverse surface which includes coupling means for receiving driving force from said drive unit to move said first piston toward said outlet, and a second piston within said cylinder, said second piston of smaller cross section that said first piston and having a surface accessible from the exterior of said diluent module, said surface having coupling means for engagement with said drive unit thereby enabling movement of said second piston in direction toward its coupling means;

said drive unit comprising a first drive rod releasably connectable to said first piston coupling means, a motor for driving said first drive rod toward said first piston for moving said first piston toward said outlet, a second drive rod releasably connectable to said second piston coupling means, means for driving said second drive rod for a predetermined distance in a direction so as to withdraw at least a portion of said second piston from said cylinder, and valve means for selectively blocking the flow of diluent from said cylinder through said outlet and said conduit.

13. The apparatus of claim 12 wherein said first piston has a bore therethrough parallel to the axis of said cylinder, said second piston being supported in said bore for movement with respect to said first piston.

14. The apparatus of claim 13 wherein said second piston and said outlet are coaxial, said valve means comprising a surface of said second piston engagable with the interior surface of said cylinder around the periphery of said outlet.

15. The apparatus of claim 13 wherein said first and second pistons are coaxial, said first drive rod being hollow and said second drive rod extending therethrough.

16. The apparatus of claim 12 wherein said first piston has a cross section of at least ten times the cross section of said second piston.

17. The apparatus of claim 12 wherein said motor is a stepping motor having an incrementally rotatably rotary member connected to linearly drive said first piston, said apparatus further including motor control means for causing a predetermined number of incremental rotations of said rotary member.

18. The apparatus of claim 17 wherein said motor control means comprise means for selecting said predetermined number of incremental rotations, thereby selecting the stroke of said first piston and the quantity of diluent dispensed by the apparatus.

19. The apparatus of claim 18 wherein said motor control means comprise means for generating a continuous train of clock pulses, counter means for counting a predetermined number of clock pulses, logic circuitry for driving said rotary member one incremental rotation for each clock pulse thus counted, and means for selecting the maximum number of clock pulses countable by said counting means; whereby said last mentioned means enable selection of the desired number of incremental rotations of said rotary member, thereby selecting the stroke of said first piston and the quantity of diluent dispensed by the apparatus.

20. Sample diluting apparatus comprising:

first piston means for aspirating a sample into said apparatus;

electromechanical means which, when energized, moves said first piston means to aspirate a sample;

second piston means for dispensing diluent from said apparatus;

stepping motor means for advancing said second piston means to dispense diluent;

a clock signal source;

multi-decade switch means settable to a preselectable value;

a multi-decade digital counter means;

gate means for selectively applying said clock signal to said counter means and to said stepping motor for advancing said diluent piston;

a first flip-flop which, when set, effects energization of said electromechanical means;

a second flip-flop which, when set, controls said gate means to energize said stepping motor;

circuit means for resetting said first flip-flop when said stepping motor is energized; and control circuit means interconnected with said counter means and said switch means for resetting said second flip-flop when the count value equals said preselected value, whereby, after the aspiration of a sample, a preselectable quantity of diluent is dispensed with the sample.

* * * * *